United States Patent [19]

Frater et al.

[11] 3,957,878

[45] May 18, 1976

[54] TRICYCLIC KETONES

[75] Inventors: Georg Frater, Greifensee; Hans Greuter, Horgen; Hans Schmid, Schwerzenbach, all of Switzerland

[73] Assignee: Hoffmann-La Roche Inc., Nutley, N.J.

[22] Filed: Aug. 29, 1975

[21] Appl. No.: 608,946

Related U.S. Application Data

[62] Division of Ser. No. 460,395, April 12, 1974.

[30] Foreign Application Priority Data

Nov. 12, 1971 Switzerland.................. 16517/71

[52] U.S. Cl. ........................ 260/586 G; 252/89 R; 252/108; 252/522; 260/586 C; 424/63; 424/69

[51] Int. Cl.$^2$.................................... C07C 49/54
[58] Field of Search............................ 260/586 G

[56] References Cited
UNITED STATES PATENTS

| | | | |
|---|---|---|---|
| 3,678,119 | 7/1972 | Kitchens et al. | 260/586 G |
| 3,711,553 | 1/1973 | Schmid et al. | 260/586 G |

*Primary Examiner*—Norman Morgenstern
*Attorney, Agent, or Firm*—Samuel L. Welt; Bernard S. Leon; Richard A. Gaither

[57] ABSTRACT

Tricyclo [5,4,0,0$^{3,9}$] undeca-5,10-dien-2-ones and tricyclo [5,4,0,0$^{3,8}$] undeca-5,9-dien-2-ones which are useful in the perfumary art and a process for their preparation from phenols and cyclohexenones.

6 Claims, No Drawings

TRICYCLIC KETONES

This is a division, of application Ser. No. 460,395 filed Apr. 12, 1974, entitled "TRICYCLIC KETONES."

Summary of the Invention

This invention relates to tricyclo ketones selected from the group consisting of the formula:

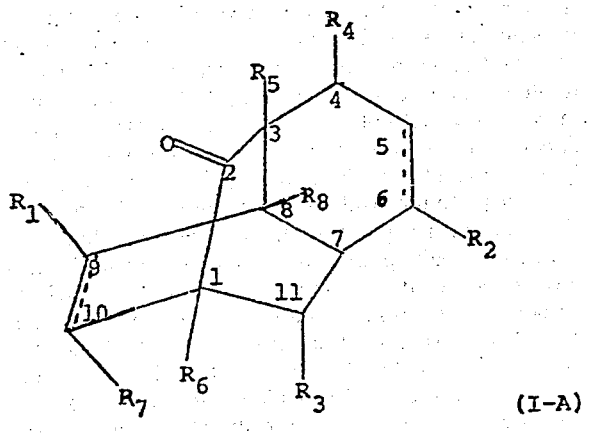

(I-A)

and

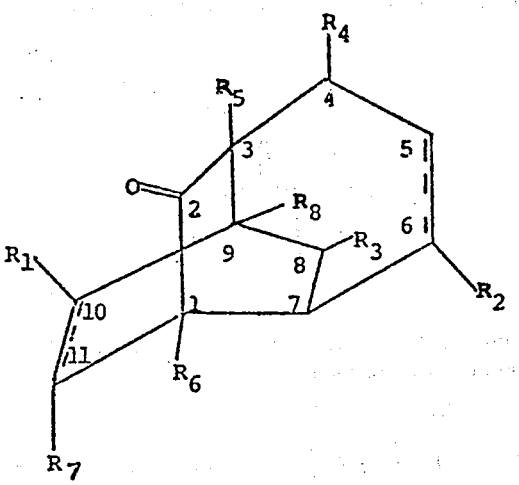

(I-B)

wherein $R_1$, $R_7$ and $R_8$ are independently selected from the group consisting of lower alkyl, hydrogen and lower alkoxy; $R_2$ is a hydrogen atom, lower alkyl or lower alkenyl; $R_3$ and $R_4$ are independently selected from the group consisting of hydrogen or lower alkyl; $R_5$ and $R_6$ are independently lower alkyl; and wherein the dotted bond can be optionally hydrogenated.

The compounds of formula I above have a camphor-like, woody, earthy and fatty odor. The compounds of formula I above and their acid addition salts because of their fragrance are useful in the preparation of perfumes, colognes and other scented compositions.

The compounds of formula I-A and I-B can be prepared from compounds of the formula:

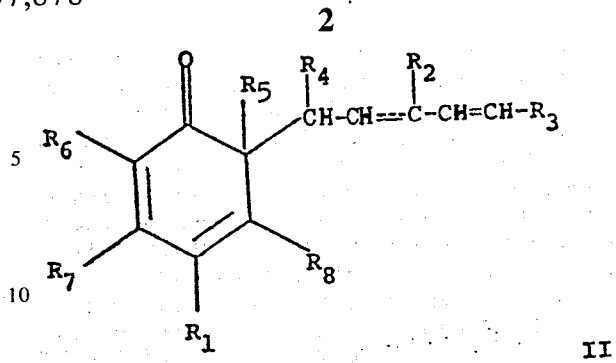

II wherein $R_1$, $R_2$, $R_3$, $R_4$, $R_5$, $R_6$, $R_7$ and $R_8$ are as above; and the dotted bond can be optionally hydrogenated.

DETAILED DESCRIPTION OF THE INVENTION

As used in this application, the expression "lower alkyl" includes both straight-chain and branched-chain hydrocarbon groups containing 1–6 carbon atoms such as methyl, ethyl, propyl, isopropyl, pentyl, 3-pentyl and the like. The alkyl moieties in the "lower alkoxy" groups are of the same kind. The expression "lower alkenyl" includes both straight-chain and branched-chain hydrocarbon groups containing 2–6 carbon atoms such as vinyl, allyl, butenyl, pentenyl and the like. The expression "halogen" includes fluorine, chlorine, bromine and iodine.

Preferred tricyclic ketones of formulae I-A and I-B above are those in which $R_2$, $R_5$ and $R_6$ each represent a lower alkyl group, preferably a methyl group. Also preferred are those compounds wherein $R_1$, $R_5$ and $R_6$ are lower alkyl, particularly methyl and those compounds where $R_1$, $R_2$, $R_5$ and $R_6$ are lower alkyl, particularly methyl. Especially preferred tricyclic ketones are:

1,3,6-trimethyl-tricyclo[5,4,0,0$^{3,9}$]undeca-5,10-dien-2-one;
1,3,6-trimethyl-tricyclic[5,3,1,0$^{3,9}$]undeca-5,9-dien-2-one;
1,3,10-trimethyl-tricyclo[5,4,0,0$^{3,9}$]undeca-5,10-dien-2-one;
1,3,9-trimethyl-tricyclo[5,3,1,0$^{3,8}$]undeca-5,9-dien-2-one;
1,3,6,10-tetramethyl-tricyclo[5,4,0,0$^{3,9}$]undeca-5,10-dien-2-one;
1,3,6,9-tetramethyl-tricyclo[5,3,1,0$^{3,8}$]undeca-5,9-dien-2-one
1,3,6-trimethyl-tricyclo[5,3,1,0$^{3,8}$]undecan-2-one;
1,3,10-trimethyl-tricyclo[5,4,0,0$^{3,9}$]undecan-2-one;
1,3,6-trimethyl-tricyclo[5,4,0,0$^{3,9}$]undecan-2-one; and
1,3,9-trimethyl-tricyclo[5,3,1,0$^{3,8}$]undecan-2-one.

The compounds of formula II above, can be cyclized to form a mixture of compounds of the formula I-A and formula I-B above by heating the compound of the formula II above. Generally, heating is carried out at a temperature of from 40° to 200° centigrade. In carrying out this reaction, temperatures of from 60° centigrade to 100° centigrade are preferred. However, the preferred temperature utilized in this cyclization will depend upon the particular starting material of formula II above which is utilized. Therefore, the preferred reaction temperature depends upon the nature of the substituents $R_1$, $R_2$, $R_3$, $R_4$, $R_5$, $R_6$, $R_7$ and $R_8$ in the compounds of the formula II above and the particular solvent. For instance, when $R_2$ in the starting material of formula II is methyl, better yields can be obtained in a shorter time than with the analogous compound of formula II where $R_2$ is hydrogen. The same is true for the reaction temperature. Thus, for best results in terms of yields, a decrease of the reaction time can be dispensed with in favor of a reduction of the reaction temperature. Also increasing the pressure will decrease the reaction time necessary to obtain optimum yields of the compounds of the formulae I-A and I-B.

While reaction temperatures of 40° centigrade to about 200° centigrade are generally utilized, the reaction can also take place at temperatures below 40° centigrade. However, at temperatures below 40° centigrade, the velocity of the reaction is slow requiring long reaction times. Thus, the utilization of temperatures below 40° centigrade makes the process not practical for large scale purposes.

The compounds of formulae I-A and I-B are formed from the compounds of the formula II by heating the compounds of the formula II in an in an inert organic solvent. In carrying out this reaction, any conventional inert organic solvent can be utilized. Generally, it is preferred to utilize inert organic solvents boiling above 40° centigrade. Among the preferred inert organic solvents are hydrocarbons such as hexane, octane, decane, benzene, toluene, etc.; halogenated hydrocarbons such as chloroform, methylenechloride, carbontetrachloride and chlorobenzene; ethers such as dioxane, tetrahydrofuran and anisole; amines such as aniline, dimethylaniline, triethylamine, pyridine, and quinoline; amides such as dimethylformamide, tetramethylurea or hexamethylphosphoric acid triamide; nitriles such as benzonitrile, acetonitrile, etc.; esters such as ethylacetate, butylacetate, etc.; ketones such as acetone, diethylketone and cyclohexanone; or a similar inert organic solvent such as dimethylsulfoxide, tetrahydrothiophene dioxide. When a low-boiling solvent is used, heating is conveniently carried out in an autoclave or a bomb tube so that the temperature can be raised in order to avoid unnecessary long reacting times.

In carrying out this reaction, it is generally best to avoid temperatures above 200° centigrade. This is true since at high temperatures decomposition of the starting material and/or the product can set in.

If desired, the process can be carried out in the presence of a Lewis acid. Any conventional Lewis acid can be utilized in carrying out the process Examples of Lewis acids which can be used are the protons, aluminum chloride, zinc chloride, tin tetrachloride, antimony chloride, iron trichloride, boron trifluoride, boron trifluoride etherate, etc. It is frequently advantageous to use as the proton donator a phenol corresponding to the starting material of formula II.

By heating the compound of formula II, a mixture of the compound of the formulae I-A and I-B is formed. The separation of this mixture into the individual components can be carried out by conventional means such as chromatography. Any conventional method of chromatography can be utilized to carry out this separation. A preferred method is by chromatography on silica gel with hexane/ethyl acetate (8:2 parts by volume) being an especially preferred elution agent. The mixture can also be separated by distillation. Any conventional method of distillation such as distillation in a high vacuum can be utilized. The tricyclic ketone of formula I-B can be obtained in pure form by crystallization from saturated hydrocarbons such as pentane or hexane. It is preferred to carry out the chromatography or distillation step after the major amount of the tricyclic ketone of formula I-B has been crystallized. By this procedure of crystallization, an enrichment of the tricyclic ketone of formula I-A in the mixture is accomplished prior to preparation by chromatography or distillation.

Where the tricyclic ketone of formula I-A or formula I-B contains at least one double bond, this compound may, if desired, be hydrogenated in the presence of a noble metal catalyst. Any conventional noble metal hydrogenation catalyst can be utilized for this purpose. In carrying out this hydrogenation, the appropriate tricyclic ketone of formula I-A or formula I-B can be dissolved in an inert organic solvent, and the mixture treated with a noble metal catalyst. Any conventional inert organic solvent can be utilized for this purpose. Among the preferred noble metal hydrogenation catalysts are included platinum oxide, platinum black, mixtures of platinum oxide and platinum black, rhodium alone or on a support such as carbon or aluminum oxide. Especially preferred as a catalyst for use in this process is palladium, alone or on a support such as carbon. The hydrogen is introduced in the usual manner and the hydrogenation terminated after the uptake of one or two moles of hydrogen. If the hydrogenation of a tricyclic ketone of formula I-B is interrupted after the uptake of one mole of hydrogen, then only the double bond in the 10,11-positions will have been saturated.

The compounds of formula II are prepared by reacting an alkali metal salt of a phenol of the formula:

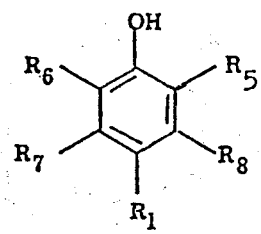

III wherein $R_1$, $R_5$, $R_6$, $R_7$ and $R_8$ are as above; with a compound of the formula:

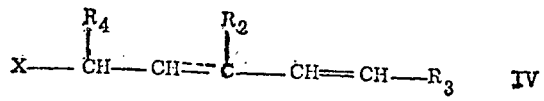

IV wherein $R_2$, $R_3$, and $R_4$ are as above; and X is chlorine, bromine, iodine or aryl sulfonyloxy or lower alkyl sulfonyloxy.

In carrying out this reaction, any conventional inert organic solvent can be used as the reaction medium. Among the preferred inert organic solvents are included aromatic hydrocarbons such as benzene, chlorobenzene and toluene. Among conventional inorganic bases which can be utilized to form the salt of compound III are included alkali metals such as sodium and potassium, and alkali metal hydrides such as sodium hydride.

According to a preferred embodiment of carrying out this reaction a phenol of formula III is dissolved, for example, in benzene and the solution treated with sodium hydride. After salt-formation has occurred, a compound of formula IV is introduced and the mixture is stirred for several hours at a temperature between 0 degrees centigrade and 40 degrees centigrade. Thereafter, the reaction mixture is poured on to water and shaken out with a strong base in order to remove the phenolic constituents. The organic phase is evaporated and the residue purified in the usual manner. As will be evident from the foregoing, the symbol X in formula IV stands for a leaving atom or group. Preferably, X stands for a bromine atom or a tosyloxy or mesyloxy group.

The stereochemistry (cis/trans isomerism) of the side-chain in a compound of formula II is not critical. All isomers can be used as the starting material.

Compounds of formula II in which the bond denoted by the broken line is hydrogenated need not be isolated but are used directly in situ as the starting material.

The tricyclic ketones of formulae I-A and I-B provided by the present invention possess particular odorant properties, their odor being camphor-like, woody, earthy and fatty.

The compounds of formulae I-A and I-B are utilized to impart fragrance to various materials such as cosmetics, perfume oils, soaps, lotions, detergents, etc. These compounds are incorporated into various materials in olfactory amounts to impart a fragrance to the material. Also, these scented compositions can contain conventional perfume carriers and perfume diluents. Any conventional perfume carrier and perfume diluent can be utilized in preparing scented compositions in accordance with this invention.

The tricyclic ketones of formulae I-A and I-B can be used in the manufacture of a wide variety of odorant compositions. They can be used, in particular as components of perfume bases for modern lines (e.g., for bases of hay-, tobacco-or honey-like character) as well as for fougere, chypre and lavender bases. Furthermore, the character of compositions having, for example, flower notes, especially hyacinth, gardenia, violet and lavender notes, can be altered or intensified with the aid of the present tricyclic ketones. These tricyclic ketones harmonize well in compositions with coumarins, ionones and rare wood essences such as vetiver oil, sandalwood oil or patchouli oil. The tricyclic ketones of formulae I-A and I-B also possess fixative properties.

The amounts in which the tricyclic ketones of formulae I-A and I-B can be used in odorant compositions vary within wide limits. In perfume bases they can be used, for example, in amounts of about 2–40 weight percent and in finished products such as perfumes, lotions, etc., they can be present in an amount of from about 1–5 percent. For the perfuming of technical products (e.g., solid and liquid detergents, synthetic washing agents, aerosols or cosmetic products of all kinds such as soaps), there can in general be used about 0.1–0.3 weight percent (in the case of washing agents) or about 0.8–2 percent (in the case of soaps) of such perfume bases.

Accordingly, it will be appreciated that the present invention also includes within its scope an odorant composition which contains as an essential odor-imparting ingredient or essential odor-imparting ingredients one or more of the tricyclic ketones of formula I-A and/or formula I-B hereinbefore. Further, this invention also includes a method of imparting an odor to materials by applying thereto or incorporating therein an odor-imparting amount of one or more of the tricyclic ketones of formulae I-A and/or I-B hereinbefore or an odorant composition as hereinbefore defined. the following examples are illustrative but not limitative of the invention. All temperatures are in degrees centigrade.

EXAMPLE 1

5 g of 6-(3-methyl-penta-2,4-dienyl)-2,6-dimethylcyclohexa-2,4-dien-1-one are dissolved in 25 ml of benzene and treated with 5 g of 2,6-dimethylphenol. The mixture is heated at reflux for 6 hours. After cooling to room temperature, the mixture is shaken portionwise with a solution of 36 g of potassium hydroxide, 25 ml of water and 100 ml of methanol. The organic phase is concentrated and the residue distilled at 70°–90°C/0.03 mmHg. The distillate contains 1,3,6-trimethyl-tricyclo[5,4,0,0$^{3,9}$]undeca-5,10-dien-2-one and 1,3,6-trimethyl-tricyclo[5,3,1,0$^{3,8}$]undeca-5,9-dien-2-one in the approximate proportion of 3:1 parts by volume.

The 3:1 mixture is dissolved in equal parts by volume of hexane and cooled to −30°C. The first-named solid tricyclic ketone separates out to a large extent with scratching. Concentration of the filtrate and repetition of this operation yields further crystals of this tricyclic ketone. The composition of the mixture of the aforementioned tricyclic ketones thereby changes from 3:1 parts by volume to approximately 1:3 parts by volume. The ultimate separation is carried out by chromatography on silicagel using hexane/ethyl acetate (8:2 parts by volume) as the elution agent. There are thus obtained 1,3,6-trimethyltricyclo[5,4,0,0$^{3,9}$]undeca-5,10-dien-2-one of melting point 54°–55°C and 1,3,6trimethyl-tricyclo[5,3,1,0$^{3,8}$]undeca-5,9dien-2-one of boiling point 70°–75°C/0.03 mmHg.

EXAMPLE 2

By the procedure of Example 1 6-(penta-2,4-dienyl)-2,4,6-trimethyl-cyclohexa-2,4dien-1-one is converted to 1,3,10-trimethyl-tricyclo[5,4,0,0$^{3,9}$]-undeca-5,10-dien-2-one of melting point 49°–50°C and 1,3,9-trimethyltricyclo[5,3,1,0$^{3,8}$]undeca-5,9-dien-2-one of boiling point 70°–75°C/0.03 mmHg (reaction time 48 hours).

EXAMPLE 3

By the procedure of Example 1 6-(3-methyl-penta-2,4-dienyl)-2,4,6-trimethyl-cyclohexa-2,4-dien-1-one is converted to 1,3,6,10-tetramethyl-tricyclo[5,4,0,0$^{3,9}$]undeca-5,10-dien-2-one of melting point 83°–86°C and 1,3,6,9-tetramethyl-tricyclo[5,3,1,0$^{3,8}$]undeca-5.9-dien-2-one of boiling point 70°–75°C/0.03 mmHg (reaction time 12 hours).

EXAMPLE 4

A 1 molar solution of 2,6-dimethylphenol in benzene is treated with sodium hydride and, after completion of the hydrogen evolution, the mixture is treated with a 10 percent molar excess of 3-methyl-penta-2,4-dienyl 1-bromide. After stirring overnight at 0°–5°C, the reaction mixture is taken up in diethyl ether and shaken with water, 10 percent by weight aqueous potassium hydroxide solution with water. The dried organic phase contains the 6-(3-methyl-penta-2,4-dienyl)-2,6-dimethyl-cyclohexa-2,4-dien-1-one which accures in 80–90 percent yield. This dienone can be stored in solution at −10°C, but it is unstable in concentrated form and at higher temperatures. [U.V. in n-hexane: maxima at 2300A ($\epsilon$ = 22,000) and 3050A ($\epsilon$ = 4270)].

EXAMPLE 5

By the procedure of Example 4
2,4,6-trimethylphenol and penta-2,4-dienyl 1-bromide are reacted to form 6-(penta-2,4-dienyl)-2,4,6-trimethyl-cyclohexa-2,4-dien-1-one [U.V. in n-hexane: maxima at 2250 A ($\epsilon$ = 26200) and 3130 A ($\epsilon$ = 4460)].

EXAMPLE 6

By the procedure of Example 4
2,4,6-trimethylphenol and 3-methyl-penta-2,4-dienyl 1-bromide are reacted to form 6-(3-methyl-penta-2,4-dienyl)-2,4,6-trimethylcyclohexa-2,4-dien-1-one: [U.V. in n-hexane: maxima at 2290 A ($\epsilon$ = 2350) and 3100 A ($\epsilon$ = 4400)].

EXAMPLE 7

16 g of 1,3,6-trimethyl-tricyclo[5,3,1,0$^{3,8}$]undeca-5,9-dien-2-one are dissolved in 250 ml of methanol and hydrogenated in the presence of 1 g of palladium-on-carbon (5 percent). After the uptake of two mols of hydrogen, the mixture is filtered off from the catalyst, evaporated and distilled. The distillate contains 1,3,6-trimethyl-tricyclo[5,3,1,0$^{3,8}$]undeca-2-one of boiling point 68°–70°C/0.05 mmHg. This product is about a 4:1 by volume mixture of the isomers at carbon atom 6.

EXAMPLE 8

By the procedure of Example 7
1,3,10-trimethyl-tricyclo[5,4,0,0$^{3,9}$]undeca-5,10-dien-2-one is converted to 1,3,10-trimethyl-tricyclo[5,4,0,0$^{3,9}$]-undecan-2-one of boiling point 68°–70°C/0.05 mmHg.

EXAMPLE 9

By the procedure of Example 7
1,3,6-trimethyl-tricyclo[5,4,0,0$^{3,9}$]undeca-5,10-dien-2-one was converted to 1,3,6-trimethy-tricyclo[5,4,0,0$^{3,9}$]undecan-2-one of boiling point 72°–75°C/0.05 mmHg.

EXAMPLE 10

By the procedure of Example 7
1,3,9-trimethyl-tricyclo[5,3,1,0$^{3,8}$]undeca-5,9-dien-2-one was converted to 1,3,9-trimethyl-tricyclo[5,3,1,0$^{3,8}$]undecan-2-one of boiling point 68°–70°C/0.05 mmHg.

EXAMPLE 11

By the procedure of Example 7
1,3,6-trimethyl-tricyclo[5,4,0,0$^{3,9}$]undeca-5,10-dien-2-one was converted to 1,3,6-trimethyl-tricyclo[5,4,0,0$^{3,9}$]undeca-5-en-2-one boiling point 71°–73°C/0.05 mmHg. However, the hydrogenation was interrupted after the uptake on one mol of hydrogen.

EXAMPLE 12

6.8 g. of mesitol dissolved in 50 ml of benzene are treated with 2.4 g of sodium hydride (50 percent suspension in oil). After completion of the salt-formation, 8.5 g of 5-bromo-1-pentene are added thereto. The reaction mixture is heated at reflux for 24 hours, taken up in hexane and shaken with an aqueous potassium hydroxide solution (10 percent by weight) and Claisen's alkali (35 g of KOH, 25 ml of water and 100 ml of methanol). The organic phase is dried, evaporated and chromatographed on silicagel using hexane and 3 percent diethylether in hexane as the elution agent. Evaporation of the eluate and recrystallization of the residue from hexane yields 1,3,9-trimethyl-tricyclo [5,3,1,0$^{3,8}$] undeca-9-en-2-one of melting point 46°–47°C.

EXAMPLE 13

The following Example illustrates a typical odorant composition provided by the invention.

Odorant composition (Fougere type) containing 1,3,6-trimethyl-tricyclo[5,3,1,0$^{3,8}$]undeca-5,9-dien-2-one.

---

| | |
|---|---|
| 50 | Sandelwood oil east Indian |
| 160 | Sandela Givaudan[1] |
| 30 | Coumarin |
| 20 | Patchouli oil |
| 20 | Vetiver oil Bourbon |
| 110 | Isobutyl salicylate |
| 300 | Lavender oil cultivated |
| 20 | Mousse de chene soluble CF |
| 30 | Orange oil Italian |
| 90 | Bergamotte oil Reggio |
| 5 | Aldehyde C-12 MNA 10 percent in phthalic acid diethyl ester |
| 20 | Versalide Givaudan[2] |
| 30 | Lilial Givaudan[3] |
| 10 | Aldehyde C-11 undecylenic 1 percent in phthalic acid diethyl ester |
| 10 | Geranium oil Bourbon |
| 20 | Galbanum oil 1 percent in phthalic acid diethyl ester |
| 10 | Ylang ylang oil Bourbon |
| 15 | Hydroxycitronellal |
| 50 | 1,3,6-Trimethyl-tricyclo[5,3,1,0$^{3,8}$]undeca-5,9-dien-2-one |
| 1000 | |

[1]isocamphylcyclohexanol
[2]1,1,4,4-tetramethyl-6-ethyl-7-acetyl-1,2,3,4-tetrahydronaphthalene
[3]p-t-butyl-α-methylhydrocinnamaldehyde

We claim:
1. A compound selected from the group consisting of tricyclic ketones of the formulae:

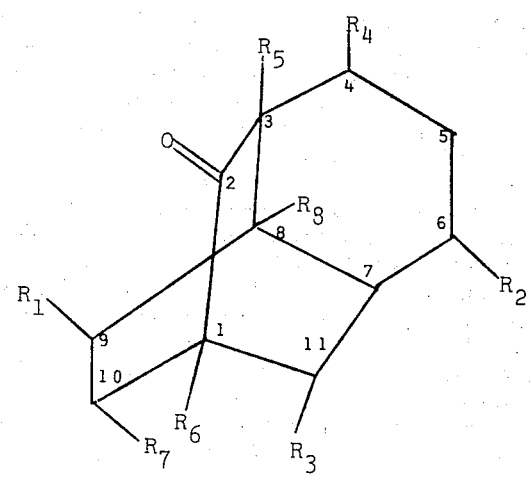

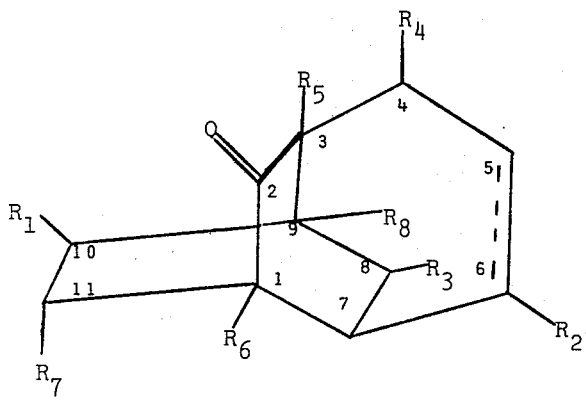

wherein $R_1$, $R_7$ and $R_8$ are independently selected from the group consisting of lower alkyl, hydrogen and lower alkoxy; $R_2$ is a hydrogen atom, lower alkyl or lower alkenyl; $R_3$ and $R_4$ are independently selected from the group consisting of hydrogen or lower alkyl; $R_5$ and $R_6$ are independently lower alkyl.

2. A compound of claim 1 wherein $R_2$, $R_5$ and $R_6$ are methyl.

3. The compound of claim 2 wherein said compound is 1,3,6-trimethyl-tricyclo[5,4,0,0$^{3,9}$]undeca-5-en-2-one.

4. The compound of claim 2 wherein said compound is 1,3,6-trimethyl-tricyclo[5,3,1,0$^{3,8}$]undecan-2-one.

5. The compound of claim 1 wherein $R_1$, $R_5$ and $R_6$ is methyl.

6. The compound of claim 5 wherein said compound is 1,3,9-trimethyl-tricyclo[5,3,1,0$^{3,8}$]undecan-2-one.

* * * * *